United States Patent [19]

Harding

[11] Patent Number: 4,956,856
[45] Date of Patent: Sep. 11, 1990

[54] ARRANGEMENT FOR EXAMINING A BODY COMPRISING A RADIATION SOURCE

[75] Inventor: Geoffrey Harding, Halstenbek, Fed. Rep. of Germany

[73] Assignee: U.S. Philips Corporation, New York, N.Y.

[21] Appl. No.: 252,955

[22] Filed: Oct. 3, 1988

[30] Foreign Application Priority Data

Oct. 5, 1987 [DE] Fed. Rep. of Germany ....... 3733599
Jun. 10, 1988 [DE] Fed. Rep. of Germany ....... 3819739

[51] Int. Cl.⁵ .......................................... G01N 23/201
[52] U.S. Cl. ........................................ 378/88; 378/86; 378/87; 378/89
[58] Field of Search .................. 378/87, 88, 86, 89, 378/90, 6, 7, 62

[56] References Cited

U.S. PATENT DOCUMENTS

| | | | |
|---|---|---|---|
| 4,020,346 | 4/1977 | Dennis | 378/95 |
| 4,123,654 | 10/1978 | Reiss et al. | 378/87 |
| 4,750,196 | 6/1988 | Harding | 378/87 |
| 4,751,722 | 6/1988 | Harding et al. | 378/88 |
| 4,754,469 | 6/1988 | Harding et al. | 378/86 |

FOREIGN PATENT DOCUMENTS

2461877 7/1976 Fed. Rep. of Germany ........ 378/87

Primary Examiner—Carolyn E. Fields
Assistant Examiner—David P. Porta
Attorney, Agent, or Firm—Paul R. Miller

[57] ABSTRACT

The invention relates to an arrangement for examining a body comprising a radiation source for producing a primary beam of small cross-section, means for producing a relative displacement between the body on the one hand and the primary beam on the other hand, a detector device sensing the radiation elastically scattered at small scattering angles and means for determining the scattering angle and or the momentum. In an embodiment, a spatial resolution in the direction of the primary beam can be obtained in that several diaphragm lamellae are arranged between the body and the detector device in such a manner that scattered radiation from different sections of the primary beam each time strikes different strips on the surface of the detector device and in that the detector has a lateral resolution in the longitudinal direction of the strips. In another embodiment, a gamma camera is employed as the detector device.

12 Claims, 6 Drawing Sheets

ARRANGEMENT FOR EXAMINING A BODY COMPRISING A RADIATION SOURCE

The invention relates to an arrangement for examining a body comprising a radiation source for producing a primary beam of small cross-section, means for producing a relative displacement between the body on the one hand and the primary beam on the other hand, a detector system sensing the radiation elastically scattered at small scattering angles in scattering angle and/or in (momentum) impulse.

Such an arrangement is known from European Patent Application No. EP 153786. There, for different areas of the body, the intensity of the scattered radiation can be determined as a function of the scattering angle and of the impulse, respectively, giving statements about the chemical condition of the irradiated substance at the respective area. The known arrangement permits, however, only determining the physical composition in the two directions perpendicular to the primary beam. In the direction of the primary beam a differentiation is not possible.

However, in many cases it is desirable also to determine the physical composition in the direction of the primary beam. If, for example, it should be checked whether a given substance is present in a piece of luggage, such a determination should be effected tridimensionally.

The present invention has therefore for its object to construct an arrangement of the kind mentioned in the opening paragraph in such a manner that the intensity of elastically scattered radiation can be determined also in the direction of the primary beam as a function of the pulse so as to be spatially resolved.

According to the invention, this object is achieved in that means for a mutual movement between the body to be examined and a primary beam and the detector system are adapted to one another in such a manner that scattered radiation from different sections of the primary beam strikes a measuring surface of the detector system along different strips and that the detector system has a lateral resolution in a longitudinal direction of the strips.

Each of the strips on the measuring surface of the detector device can therefore only be struck by scattered radiation which originates from a given section of the primary beam within the body. The detection device can sense only that scattered radiation which lies in a given angle range. The smallest scattering angle that can be sensed depends upon the inclination of the diaphragm lamellae to the primary beam. If the scattered radiation emanates in a plane arranged perpendicularly to the diaphragm lamellae, it can reach one of these strips at this scattering angle. Scattered radiation emanating at a larger scattering angle is also sensed by the detection device if it passes at an angle to the plane. Thus, each strip on the measuring surface senses a part of the scattered radiation emanating at the associated section of the primary beam in a given angle range. In order that for this section the scattering intensity can be determined as a function of the scattering angle and of the pulse carry, respectively, the detector device must have a spatial resolution in the longitudinal direction of the strips. A suitable detector device may comprise several detector lines extending in the strip direction, but a detector device having a large surface area may also be used. If the radiation source produces a polychromatic X-ray or gamma radiation, the detector device must additionally have an energy resolution, that is to say it must be able to determine the energy of the X-ray quants or radiation particle energy measured each time.

In a suitable further embodiment it is preferred that the detector device is a gamma camera arranged outside the primary beam but aligned with respect to the primary beam in such a manner that the normal to its entrance surface intersects the primary beam at an angle different from zero. Thus, the detector device used is a gamma camera, which is arranged in such a manner outside the primary beam that it is struck by the scattered radiation passing through the diaphragm lamellae. Since the inclination angle of the diaphragm lamellae with respect to the primary beams must be very small, for example 2°, the scattered radiation from the individual sections of the primary beam would be projected onto comparatively narrow strips with the use of a gamma camera arranged with its measuring surface at right angles to the primary beam. Because of the limited spatial resolution of a gamma camera, it would then hardly be possible to evaluate individually the separate strips—and hence the separate sections of the primary beam. Due to the fact that the normal to the measuring surface of the gamma camera intersects the primary beam at an angle different from zero, which must be smaller than 90°, but not too much smaller than this value, the scattered radiation from the separate sections is projected onto comparatively wide strips on the gamma camera, which in spite of their limited resolution can be evaluated individually.

In practice, it is inevitable—and with a view to the signal-to-noise ratio with comparatively short measuring times even required—that the primary beam has finite dimensions. However, as a result, an additional inaccuracy is obtained because a point on the surface of the detector device is struck by the scattered radiation from the sectional area of the primary beam in a plane at right angles thereto within the body not at an accurately defined angle, but at an angle range whose dimensions depend upon the dimensions of the cross-section of the primary beam. In order that these inaccuracies due to the finite dimensions of the primary beam cross-section remain as small as possible with a given cross-sectional area, in a further embodiment of the invention it is preferred that the cross-section of the primary beam has substantially approximately the form of an ellipse, whose longitudinal axis extends parallel to the direction of the strips and is twice the transverse axis.

In a further embodiment of the invention, several diaphragm lamellae are arranged between the body and the detector device in such a manner that scattered radiation from different sections of the primary beam each time strikes different strips on the measuring surface of the detector device and in that the detector device has a lateral resolution in the longitudinal direction of the strips.

The invention will now be described more fully with reference to the accompanying drawings, in which:

FIG. 5 shows a second embodiment, and
FIGS. 6 and 7. shows the geometric conditions in the arrangement of FIG. 5 in orthogonal planes containing the primary beam.

Figure 1:
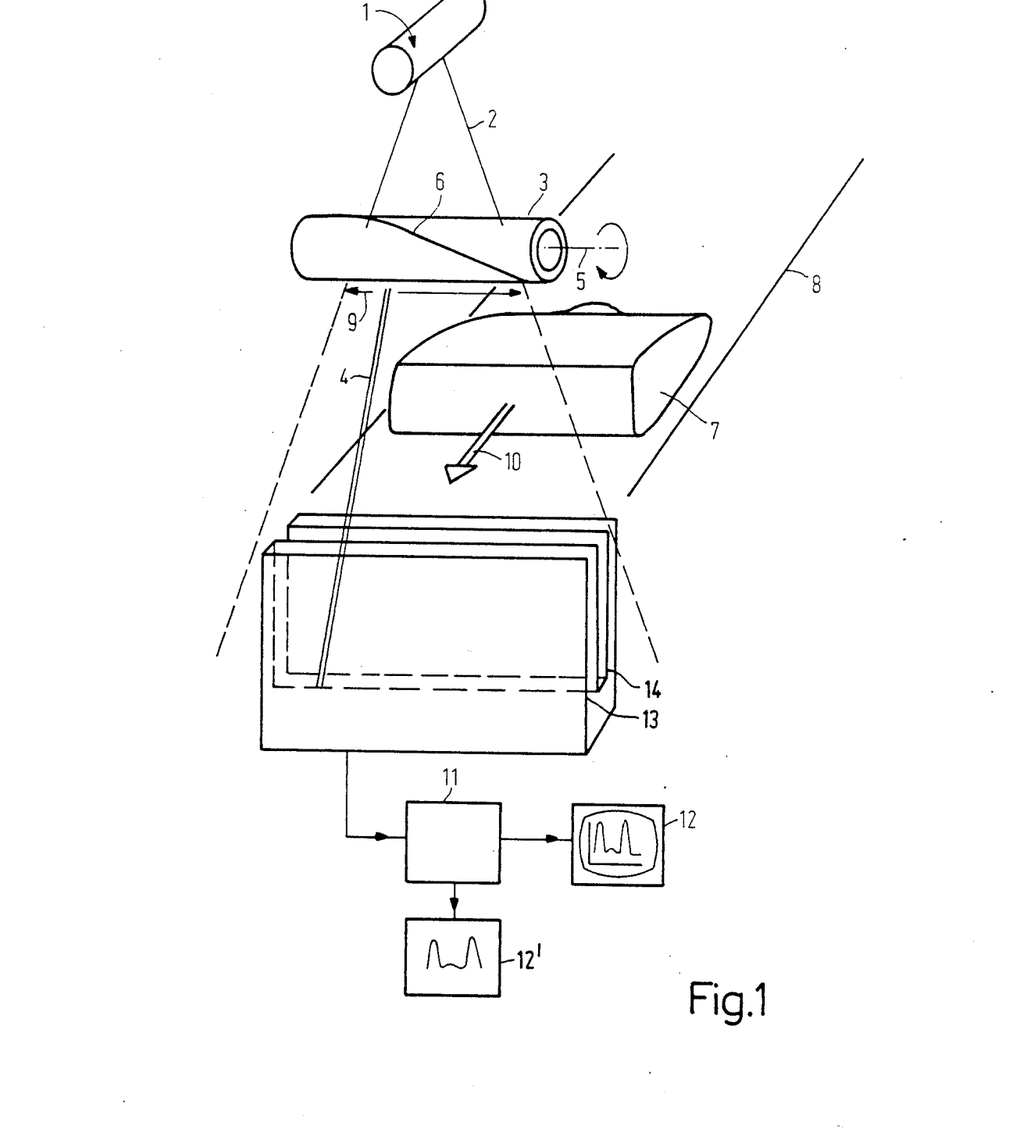
FIG. 1 shows diagrammatically a first embodiment.

FIG. 1 shows a luggage control system which permits indicating a given substance, for example an explosive, in the piece of a luggage. This device comprises an X-ray radiator 1, which produces by means of a slot diaphragm (not shown) a fan-shaped beam of radiation 2. The fanshaped beam of radiation 2 strikes a diaphragm device 3, which forms from the fan-shaped radiation beam a beam 4 of small cross-section (pencil beam), which performs a reciprocating movement and is designated hereinafter as primary beam. The device comprises a hollows roller 3, which consists of radiation-absorbing material and is provided with two spiral-shaped slots 6, which are relatively offset along their circumference by 180° such that only one can be seen in the drawing. The X-ray radiation penetrates on the side of the hollow roller 3 facing the radiation source 1 through the slot situated there at a given area and leaves it on the opposite side through the other slot. When the hollow roller 3 is rotated about its rotary shaft 5 by means of an electric motor (not shown), the area at which a ray from the fan-shaped radiation beam 2 penetrates through the hollow roller 3 performs a reciprocating movement so that the primary beam 4 emanating from the hollow roller 3 is moved in a reciprocating manner within the plane given by the fan-shaped beam 2.

The device described for producing a beam performing a reciprocating movement is known per se (compare German Offenleggenschrrift DE-OS 34.43.095). However, instead thereof, a rotating disk of a material not transparent to X-ray radiation, which is provided with four radial slots relatively offset by 90° may be used, which rotates about a shaft located outside the fan-shaped beam and parallel thereto.

The primary beam 4 performing a reciprocating movement within the vertical plane of the fan-shaped beam 4 traverses a body 7, in this case a piece of luggage to be controlled, which is transported on a conveyor belt 8. The direction of the reciprocating movement of the primary beam 4 indicated by the arrow 9 and the transport direction of the conveyor belt indicated by the arrow 10 are at right angles to each other. The speeds of the conveyor belt 8 and of the reciprocating movement of the primary beam 4 are adapted to each other in such a manner that the piece of luggage 7 is transported only over a compartively small distance, for example over a path corresponding to the thickness of the primary beam, within the time interval in which the primary beam traverses once its area of movement indicated by the broken lines. Thus, it is achieved that the piece of luggage 7 is scanned completely by the primary beam 4.

Below the conveyor belt 8 is situated a detector arrangement. The latter comprises at least one detector located outside the vertical plane of the fan-shaped beam 2 in a plane parallel thereto and has an elongated form and is arranged also horizontally, but at right angles to the arrow 10. Moreover, in the plane of the fan-shaped beam is further arranged an also elongated detector, which measures the intensity of the primary radiation and hence the absorption of the X-ray radiation by the object.

The detector output signals are digitized in a circuit 11 and the variation of the scattering intensity is standardized on the intensity of the primary beam determined as a function of the impulse and is indicated on a monitor 12 in a manner to be described hereinafter. At the same time, this variation is compared with a variation which is stored in a memory 12, and represents the scattering characteristics of the substance to be indicated. If the two variations are in conformity with each other or deviate only slightly from each other, this is an indication that the substance searched for is present in the piece of luggage, which is signalled by an additional indication device (not shown).

Figure 2:
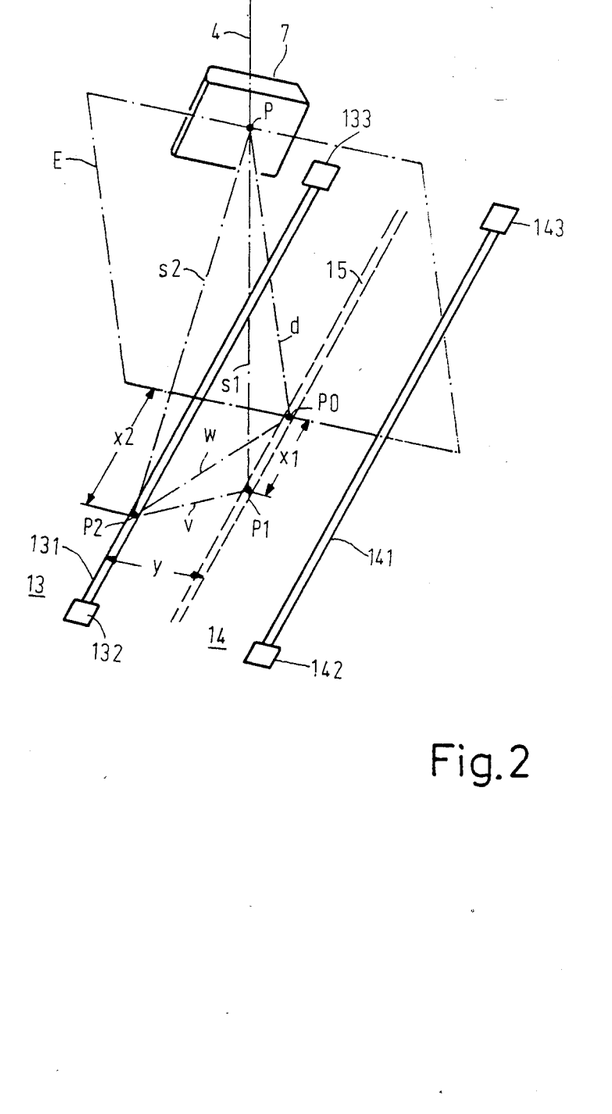
FIG. 2 shows diagrammatically a bottom view.

FIG. 2 shows two detectors 13 and 14 intended to detect the scattered radiation. These detectors each comprise an elongated sodium iodide scintillator 131 and 141, respectively, at whose both ends is each time arranged a photomultiplicator 132, 133 and 142, 143, respectively. The two scintillators 131 and 141 extend parallel to the plane of the fan-shaped beam 2 and perpendicularly to the direction of movement 10 of the piece of luggage 7. They define a plane which is at right angles to the plane of the fan-shaped beam 2. In FIG. 2, the line 15 indicates the strip in which the primary beam 4 can intersect the plane of the detectors of scattered radiation.

If one of the detectors is struck accurately at the center by an X-ray quant or a gamma quant, the photomultiplicators 132 and 133 and 142 and 143, respectively, supply equally large signals if it is assumed that the photomuliplicators are identically constructed. If on the contrary one of the scintillator strips 131 or 141 is struck outside the center by an X-ray quant or gamma quant, the output signal of the photomultiplicator (for example 132) located in the proximity of the striking point of the X-ray quant or gamma quant is larger than that of the farther remote photomultiplicator 133. Thus, the position of the striking point of a gamma quant can be determined from the difference of the signals of the two photomultiplicators 132, 133. On the other side, the sum of the amplitudes of the two photomultiplicator signals is at least approximately proportional to the energy of the incident X-ray or gamma quants. Thus, also the energy of the X-ray or gamma quants striking the detector can be determined from the sum of the amplitudes of the photomultiplicator signals.

In FIG. 2, different geometric auxiliary quantities are shown, by means of which it is possible to determine the scattering angle of a scattered X-ray quant detected by one of the detectors.

Let it be assumed that the primary beam 4 has at a given instant such a position that it intersects the plane defined by the detectors 13 and 14 in the point P1. Let it further be assumed that at the same instant the detector 13 is struck by a scattered X-ray quant in the point P2. The point P, in which the primary beam intersects the body 7, is then indicated by P. In itself the primary beam intersects the body 7 not in a point, but in a section of a straight line. If, however, the length of this section is small as compared with the distance of the body 7 from the detectors 13 and 14 detecting the scattered radiation, on good approximation the center point of this section can be used as the point P.

In FIG. 2, E indicates a plane which contains the point P and extends at right angles to the two detectors 13 and 14. This plane intersects the strip 15, in which the primary beam 4 is moved, in the point PO.

If the distance of the point P2 from the point P is designated by $s_2$, the distance of the point P1 from the point P is designated by $s_1$ and the distance between the two points P1 and P2 is designated by v, the scattering angle $\beta$, at which the X-ray quant striking in the point P2 has been scattered in the point P can be determined from the formula:

$$\cos\beta = \frac{s1^2 + s2^2 - v^2}{2s1s2} \quad (1)$$

The distance s1 depends upon the instantaneous position of the primary beam. If the (fixed) distance of the point PO from the point P is designated by d and the distance (variable with time) of the point P1 from the point PO is designated by x1, s1 can be determined by means of the following equation:

$$s1^2 = d^2 + x1^2 \quad (2)$$

where s1 is determined by the position of the primary beam or by the respective position of the hollow roller 3 and this also applies to x1. The circuit 11 could therefore comprise a read-only memory, in which the precalculated values x1, s1 are stored for different angular positions of the hollow roller 3. However, it is also possible to measure the place x1, in which a plurality of detectors arranged beside each other, for example on the strip 15, for detecting the primary beam are used. The value x1 should then appear from the position of the detector struck each time by the primary beam.

If x2 is the distance of the point P2 from the plane E that can be determined from the difference of the detector signals supplied by the photomultiplicators 132 and 133 and if y is the (fixedly determined) distance of the scintillator strip 131 from the plane 2 of the fan-shaped beam 9, the distance w of the point P2 from the point PO can be determined according to the equation:

$$w^2 = x2^2 + y^2 \quad (3)$$

Thus, for the distance of the point P2 from the point P there is obtained:

$$s2^2 = d^2 + w^2 \quad (4)$$

The distance v between the points P2 and P1 is obtained from the equation:

$$v^2 = (x2 - x1)^2 + y^2 \quad (5)$$

The scattering angle $\beta$ can therefore be determined according to the equations (1) to (5) from the position of the point P2 derived from the output signals of the photomultiplicators 132 and 133, in which point the scintillator 131 is struck by a scattered X-ray quant, and from the position of the primary beam at the instant at which the scattering process takes place.

The impulse X produced by the scattering process can be calculated from the scattering angle $\beta$ according to the equation:

$$X = E \sin(\beta/2)/(hc) \quad (6)$$

where E is the energy of the scattered X-ray quant, which is obtained from the sum of the amplitudes of the output signals of the photomultiplicators 132, 133; h is the Planck efficiency quant and c is the light velocity. Since elastically scattered radiation emanates at only small scattering angles, sin $\beta$ can be replaced by $\beta$, while combining the constants to a new constant k, there is obtained:

$$X = kE\beta \quad (7)$$

The described calculation of the impulse is repeated for each scattering process, which is recorded by one of the detectors 13 or 14 intended for the scattered radiation. The number of scattering processes per unit time (i.e. the scattering intensity) is then determined, which are associated with a given impulse and a given impulse range, respectively. Each scattering process which is recorded within a time interval, in which the primary beam is shifted by a path corresponding to its thickness, is associated with a given volume element in the piece of luggage. The scattering characteristic for this volume element is obtained from the dependence of the scattering processes counted in this time interval upon the impulse X. This scattering characteristic is compared with a stored characteristic and in dependence upon the result of this comparison, as the case may be, an indication device is activated.

When the primary beam is further shifted, the scattering characteristics of further volume elements of the piece of luggage situated in a plane at right angles to the transport direction (arrow 10) is examined. Subsequently, the volume elements in the planes parallel and adjacent to the plane are examined until the whole piece of luggage has been scanned continuously and bidimensionally.

It should be appreciated that the intensity of the scattered radiation also depends upon the extent to which the primary beam is absorbed by the body. In order to obtain a standardized variation independent of the absorption, the variation obtained must therefore be brought into relation with the absorption of the scattered radiation. This can be effected in that the measured scattering intensity is defined by the intensity of the primary beam behind the body 7, it being assumed that the primary beam and the scattered radiation are attenuated in the same manner by the body 7. The measurement of the intensity of the primary radiation can take place by means of a detector, which may have the same construction as the detectors 13 and 14, but which also may consist of individual detector cells arranged beside each other, as has been explained more fully hereinbefore. The detector must be arranged parallel to the detectors 13 and 14 in the plane of the fan-shaped beam 2; it may lie in the plane of the detectors 13 and 14, but may also be arranged at a greater distance from the radiation source.

If the radiation source 1 would supply monochromatic X-ray radiation, the energy of all the elastically scattered X-ray quants would be equal because the elastically scattered X-ray quants, as is known, do not lose energy during the scattering process. In this case, the calculation of the impulse according to the equations (6) and (7) would be superfluous and it would be sufficient to determine the variation of the scattering intensity and of the scattering coefficient, respectively, as a function of the scattering angle.

Figure 3:
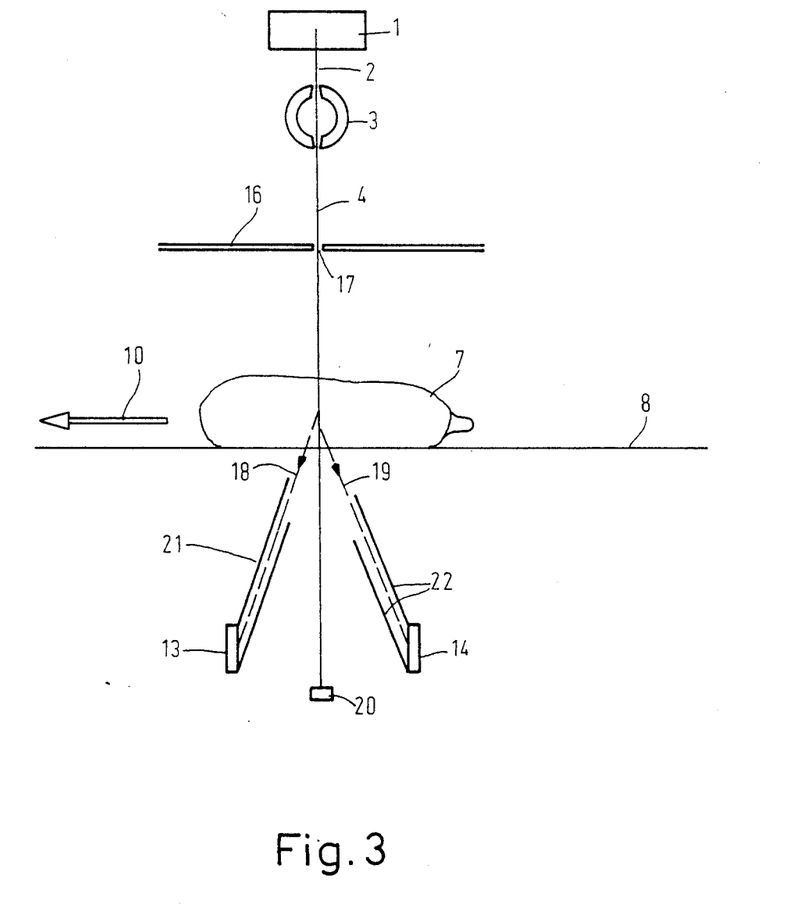
FIG. 3 shows a side elevation.

FIG. 3 shows the arrangement of FIG. 1 in a side elevation. The rotary shaft of the hollow cylinder 3 extends at right angles to the plane of the drawing and an additional diaphragm plate 16 of radiation-absorbing material having a slot 17 leaving free the plane of the fan-shaped beam is further provided between the piece of luggage 7 to be examined and the hollow roller 3. As a result, fluctuations of the thickness of the primary beam 4 as a function of the respective position x1 of the primary beam, which cannot be fully avoided in practice, can be eliminated.

As already stated, the thickness of the object 7 to be examined, which is moved in FIG. 3 in accordance with the arrow 10 from the right to the left, is not arbitrarily small. Consequently, each detector would receive scattered radiation from the whole area of the body 7 traversed by the primary beam 4. If the substance to be detected should be present only in a part of this area, its characteristic would be superimposed on the characteristic of that substance, or those substances which is or are additionally present in the primary beam. As a result, possibly the searched characteristic could be covered or marked.

In order to avoid this, beam lamellae 21 and 22 are arranged between the detectors 13 and 14 of scattered radiation and the conveyor belt 8 on which the body is transported in such a manner that the detector 13 can be struck by the scattered radiation produced in the upper part of the body—symbolically indicated by the beam 18—and the detector 14 can be struck only by the scattered radiation produced in the lower part and indicated by the broken line 19. Each of the two detectors therefore detects only the scattered radiation from a subpart of the body 7 so that the scattering characteristic determined by a detector is independent of the scattering characteristic of the substances present in the other area of the primary beam.

FIG. 3 moreover shows a detector 20 for measuring the intensity of the primary beam. It is arranged in the plane of the fan 2 and below the plane defined by the detectors 13 and 14. As already stated, the elastically scattered radiation is essentially concentrated on an angular range between 0° and 10° to the direction of the primary beam. Consequently, the detectors 13 and 14 must lie in much closer proximity to the fan-shaped beam 2 than is shown in FIG. 3.

Figure 4:
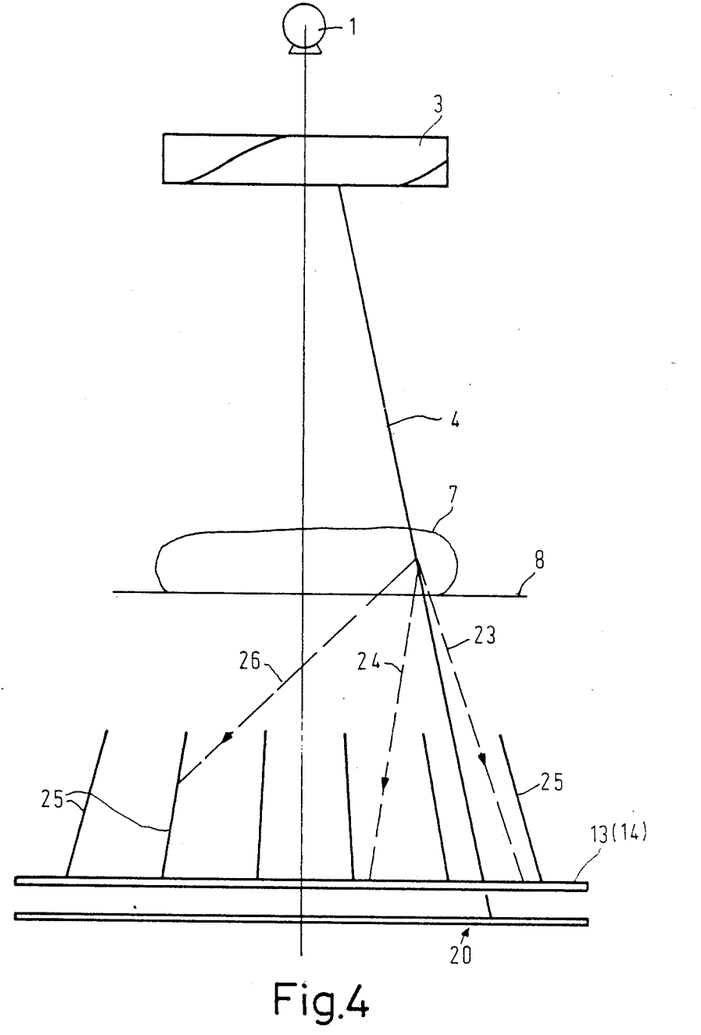
FIG. 4 shows a front elevation of the embodiment.

FIG. 4 shows the arrangement in a front elevation, in which the direction of displacement of the conveyor belt 8 is at right angles to the plane of the drawing. The lamellae 21 and 22 as well as the slot 16 are omitted for the sake of clarity. Scattered radiation lamellae 25 consisting of a material absorbing the X-ray radiation are located between the conveyor belt 8 and the detectors 13 (14) of scattered radiation. They are arranged in planes which are aligned with the X-ray radiator 1. Consequently, they do not influence the primary beam. They pass also without hindrance the scattered radiation emanating at small scattering angles—indicated in FIG. 4 by the beams 23 and 24—while they absorb the scattered radiation enamanting at larger scattering angles—as indicated by the beam 26. Since the undesired Compton scattered radiation essentially emanates at larger scattering angles, the undesired Compton scattered radiation (beam 26) is therefore suppressed by the lamellae 25, while the desired elastic scattered radiation (beams 23, 24) is substantially not influenced by the lamellae.

The application of the invention in a luggage control system was described above. However, it may also be used in examinations on human bodies, for example in the examination with respect to osteoporosis. Bones attacked by osteoporosis in fact have a scattering characteristic quite different from that of sane bones. As a result, it becomes possible to recognize the disease at an early stage.

As already stated, in the embodiment described in FIGS. 1 to 4, the detectors 13, 14 must be longer than the body to be examined. In an application for luggage control, this may lead to very long and hence also expensive detectors. With such detectors it is particularly difficult to determine the accurate striking point of an X-ray quant so that the scattering angle of this X-ray quant cannot be determined in practice with the required accuracy. In the embodiment shown in FIG. 5, which is particularly suitable for the examination of pieces of luggage, this disadvantage is avoided in that the primary beam 2 stands still relative to the detector arrangement. In this case, parts of the arrangement having the same meaning as in FIGS. 1 to 4 are designated by the same reference symbols.

The piece of luggage 7 to be examined is provided on a conveyor belt, which extends at right angles to the plane of the drawing and can be driven in a stepwise manner. The examination takes place by means of the thin primary beam 2 (pencilbeam) produced by the diaphragms 3 and 4 from the radiation beam of an X-ray radiator 1. The elastically scattered X-ray radiation—i.e. without energy loss—which is produced in the area of the primary beam 2 traversing the body 7, is measured by a gamma camera 30 with the scattered radiation produced at different depths of the body 7 being separately measured by means of a diaphragm arrangement not shown further in FIG. 5 (and FIG. 7), as will be explained below. As is indicated by arrows 35, the radiation source 1 and the gamma camera 30 can be displaced together with the diaphragms 3 and 4 disposed between the radiation source and the body 7 horizontally, i.e. at right angles to the primary beam and at right angles to the direction of displacement of the piece of luggage. Due to this double relative displacement between the object 7 and the primary beam 2, a bidimensional scanning is possible.

Figure 5:
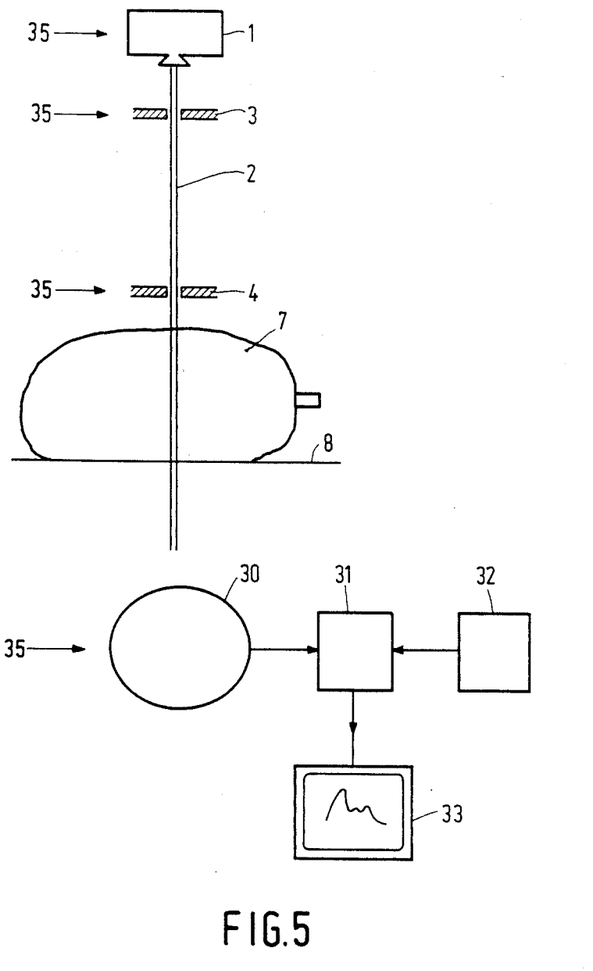

The gamma camera may have the same construction as the gamma cameras used for medical examinations. The measuring surface is then constituted by a scintillator crystal of large format and preferably of circular shape, on whose back side are arranged a number of photomultipliers according to a regular honeycomb pattern. An X-ray or a gamma quant occuring on the scintillator crystal produces light at the striking point and this light spreads within the crystal and is therefore sensed by each of the photomultipliers. The intensity of the light depends not only upon the energy of the gamma quant, but also upon the distance of the respective photomultiplier from the striking point of the gamma quant on the scintillator crystal. Therefore, both the striking point of an X-ray or a gamma quant and its energy can be determined from the output signals of all photomultipliers. Besides this spatial and energy resolution, a gamma camera operating according to this principle—developed by Anger—further has a lateral resolution, that is to say that the position and the energy of quants striking successively in time can be individually measured.

Figure 6:
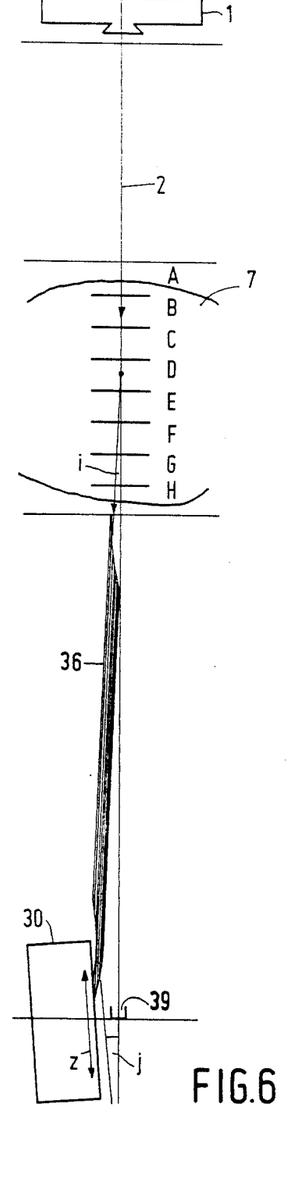

As appears from FIG. 6, a diaphragm arrangement 36 comprising a number of parallel flat diaphragm lamellae of a material strongly absorbing X-ray radiation is provided between the examination area, i.e. the area at which the body to be examined or the piece of luggage to be examined is generally present, and the gamma camera. These diaphragm lamellae lie in planes intersecting the primary beam at the examination area at an angle i of, for example, 2°, the examination area being subdivided by these points of intersection into a number of equally long sections A . . . H. The scattered radiation originating from the sections A to H at the examination area of the primary beam traverses the diaphragm arrangement 20 and strikes each time one of the strips a . . . h on the measuring surface of the scintillator crystal of the gamma camera; the radiation scattered in the section A strikes, for example, the strip a (FIG. 7); the radiation scattered in the section B strikes the strip b, etc.

Figure 7:
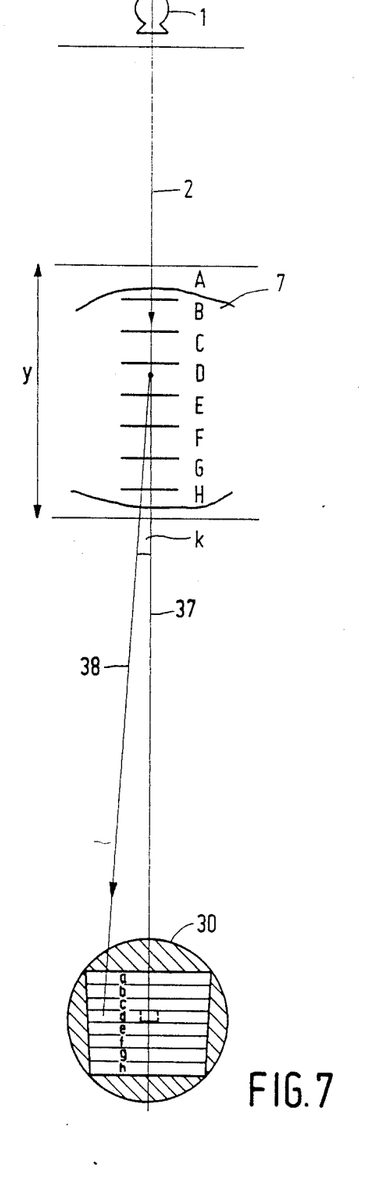

If the dimension z of the gamma camera (FIG. 6) in the direction of the strips should correspond to the thickness y of the examination area (FIG. 7), the measuring surface of the gamma camera could extend parallel to the primary beam (in this case the normal to the center of the measuring surface would intersect the primary beam perpendicularly.) Since the dimensions of the gamma camera are generally smaller, however, the camera must be inclined so that the measuring surface encloses with the primary beam an angle j different from zero (the normal intersects the primary beam in this case at an angle which is smaller than 90°). The relation then holds that:

$$z/y = i/(i+j) \tag{8}$$

If the angle j is larger than appears from the equation (8), no longer all sections A to H can be imaged on the gamma camera. If on the contrary the angle is smaller, the width of the individual strips on the gamma camera becomes smaller than is necessary so that the risk increases that gamma quants originating from a given section of the primary beam are assigned by the electronic evaluation system of the gamma camera to an adjacent strip or an adjacent section. Therefore, the inclination angle of the gamma camera would have to be proportioned in accordance with the equation (8).

A separate detector 39 measures the intensity of the primary beam 2 emanating from the body 7. This is required especially if the scattering density distribution must be reconstructed from the measured values of the gamma camera.

In practice, the primary beam 2 is not a beam in the mathematical sense, but it has a finite cross-section. The scattered radiation produced at an accurately defined depth strikes a point on the measuring surface of the detector not at a defined angle, but in a given angle range. Therefore, a scattering angle can be assigned only on approximation to a point on the strip. In order to keep as small as possible the inaccuracy determined thereby with a given cross-section, the cross-section would have to be elongated, preferably elliptical, while the major axis of the ellipse must be twice as large as the minor axis and must be parallel to the longitudinal direction of the strips.

In FIG. 7, reference numeral 37 designates a plane containing the primary beam and at right angles to the diaphragm arrangement 36 or to the plane of the drawing of FIG. 7. This plane is at the same time the plane of symmetry for each of the strips a . . . h because the normal to the center of the measuring surface of the gamma camera intersects the primary beam. The smallest scattering angle at which radiation scattered in the primary beam can reach the gamma camera is determined by the inclination of the diaphragm arrangement 36. It is i=2°. In this case, the scattered radiation passes in the plane of symmetry 37 and strikes the associated strip at its center. Besides, there is scattered radiation, which—like the scattered beam 38 shown individually in FIG. (7)—does not strike the associated strip (d) at the center, but rather extends at the edge at an angle k to the plane 37. The scattering angle associated with this scattered beam corresponds on close approximation to the root of the sum of the squares of the angles i and k as long as the angle is smaller than 10°. Thus, each point on one of the strips a . . . h is associated with a given scattering angle, the scattering angle of 2° (at the center of the strip) increasing to, for example, 6° (at the end of the strip). The associated pulse carry X has the value $$X = \beta/2L \tag{9}$$

where $\beta$ is the scattering angle and L is the wavelength which can be determined from the energy E of the individual quant measured by means of the gamma camera according to the known relation L=hc/E. (h=Planck's efficiency quantum; c speed of light).

Thus, each X-ray quant striking the measuring surface of the gamma camera can be assigned to a given section from the section A . . . H and to a given pulse carry or pulse carry range. The evaluation circuit 31, to which the output signals of the gamma camera 30 are supplied, counts correspondingly for each section and for each pulse carry range the number of the gamma quants striking per unit time. Thus, the variation of the intensity as a function of the pulse carry can be determined for each section A . . . H from the number of the quants recorded during a unit time. If one of the scattering characteristics thus obtained for the different sections corresponds to the characteristics stored in a memory 32 and characteristic of a given substance, for example an explosive, this is indicated by the evaluation circuit 31. A suitable indication circuit, for example a monitor 33, is coupled to the evaluation circuit 32.

The measurement described of the scattering characteristic of the different sections is repeated for different positions of the primary beam 2 relative to the body 7 and for the individual displacement steps of the transport belt 8 so that in the belt all volume ranges of the article 7 are checked with respect to the presence of the substance searched.

It is also possible to use for additional measuring a second diaphragm detector arrangement, which is arranged so as to be offset relative to the first arrangement by 180° (related to the primary beam). As a result, the signal-to-noise ratio can be improved and the measuring time can be shortened, respectively.

What is claimed is:

1. A radiation arrangement for examining a body comprising:
   (a) radiation source means for producing a primary radiation beam having a pencil beam cross-section,
   (b) displacement means for producing a relative displacement between a body to be examined and said primary radiation beam,
   (c) detection means for detecting radiation elastically scattered at small scattering angles by said body from said primary radiation beam, wherein said small scattering angles are approximately equal to the sine of said scattering angle, and
   (d) diaphragm means constituting a plurality of lamella disposed between said body and said detection means for directing scattered radiation at said small scattering angles from different sections of said primary radiation beam in said body to different measuring strips on a measuring surface of said detection means, said detection means having a lateral resolution in a longitudinal direction of said measuring strips, such that said detection means is position sensitive along each of said plurality of lamella, wherein said detection means includes a plurality of parallel detectors, said plurality of detectors being disposed adjacent an area of said primary radiation beam, and said detectors detecting each time said scattered radiation passing through adjacent lamellas, said small scattering angle being determined by the striking point of said scattered radiation on said detectors, and wherein reciprocating diaphragm means are disposed between said radiation source means and said body for producing said primary radiation beam in a reciprocating movement in a plane parallel to said detection means.

2. An arrangement according to claim 1, wherein said primary radiation beam has a cross-section approximately in the form of an ellipse, said ellipse having a longitudinal axis extending parallel to said measuring strips, and said ellipse having a transverse axis extending half the dimension of said longitudinal axis.

3. An arrangement according to claim 1, wherein each of said plurality of parallel detectors includes an elongated scintillation crystal having a photomultiplier at each end.

4. An arrangement according to claim 3, wherein said scintillation crystal is sodium iodide.

5. An arrangement according to claim 1, wherein said reciprocating diaphragm means includes a rotatable hollow cylinder having two spiral-shaped slots provided through the cylindrical surface, said two slots being offset about a circumference of said cylinder, said primary radiation beam passing through said two slots to form said pencil beam cross-section at one point.

6. An arrangement according to claim 1 or claim 3 or claim 5, wherein said radiation source means includes a polychromatic x-ray radiator, and wherein said detection means measures energy of said scattered radiation.

7. An arrangement according to claim 1 or claim 3 or claim 5, wherein said displacement means includes a conveyor belt, said body being arranged on said conveyor belt.

8. An arrangement according to claim 1 or claim 5, wherein said plurality of lamella are disposed beyond said body, said lamella being provided in planes aligned with said radiation source means, said planes being parallel to said longitudinal direction.

9. An arrangement according to claim 8, wherein said detection means includes a gamma camera arranged outside of said primary radiation beam, said gamma camera being aligned with respect to said primary radiation beam so that a normal to an entrance surface of said gamma camera intersects said primary radiation beam at an angle different from zero.

10. An arrangement according to claim 1 or claim 3 or claim 5, wherein a further detection means for measuring intensity of said primary radiation beam is disposed within an area traversed by said primary radiation beam beyond said body.

11. A radiation arrangement, for examining a body comprising:
(a) radiation source means for producing a primary radiation beam having a pencil beam cross-section,
(b) displacement means for producing a relative displacement between a body to be examined and said primary radiation beam,
(c) detection means for detecting radiation elastically scattered at small scattering angles by said body from said primary radiation beam, wherein said small scattering angles are approximately equal to the sine of said scattering angle, and
(d) diaphragm means constituting a plurality of lamella disposed between said body and said detection means for directing scattered radiation at said small scattering angles from different sections of said primary radiation beam in said body to different measuring strips on a measuring surface of said detection means, said detection means having a lateral resolution in a longitudinal direction of said measuring strips, such that said detection means is position sensitive along each of said plurality of lamella,
wherein said detection means includes a gamma camera arranged outside of said primary radiation beam, said gamma camera being aligned with respect to said primary radiation beam so that a normal to an entrance surface of said gamma camera intersects said primary radiation beam at an angle different from zero.

12. An arrangement according to claim 11, wherein said primary radiation beam has a cross-section approximately in the form of an ellipse, said ellipse having a longitudinal axis extending parallel to said measuring strips, and said ellipse having a transverse axis extending half the dimension of said longitudinal axis.

* * * * *